United States Patent [19]
Jackson

[11] Patent Number: 4,552,156
[45] Date of Patent: Nov. 12, 1985

[54] EXERCISE S-T SEGMENT EVALUATOR

[75] Inventor: Frank W. Jackson, Twillingate, R.D. 3, Mechanicsburg, Pa. 17055

[73] Assignee: Frank W. Jackson, Mechanicsburg, Pa.

[21] Appl. No.: 507,392

[22] Filed: Jun. 24, 1983

[51] Int. Cl.⁴ .............................................. A61B 5/02
[52] U.S. Cl. ...................................... 128/703; 33/1 C
[58] Field of Search ............................... 128/702–708; 33/1 B, 1 C

[56] References Cited

U.S. PATENT DOCUMENTS 3,868,567  2/1975  Ekstrom ............................. 128/704
3,940,692  2/1976  Neilson ........................... 128/702 X
4,170,992  10/1979  Dillman ............................. 128/702

OTHER PUBLICATIONS

Weisner et al.; "Microprocessor–Based, Portable Anesthesiology ST-Segment Analyzer"; *Proc. of 10th Ann. NW Bioengr. Conf.*, 3-1982; pp. 222-226.

Primary Examiner—Kyle L. Howell
Assistant Examiner—Angela D. Sykes
Attorney, Agent, or Firm—Eugene Chovanes

[57] ABSTRACT

An overlay device for use with an electrocardiogram and the method of use thereof, for evaluating the normalcy of the S-T segment in an exercise test program.

7 Claims, 7 Drawing Figures

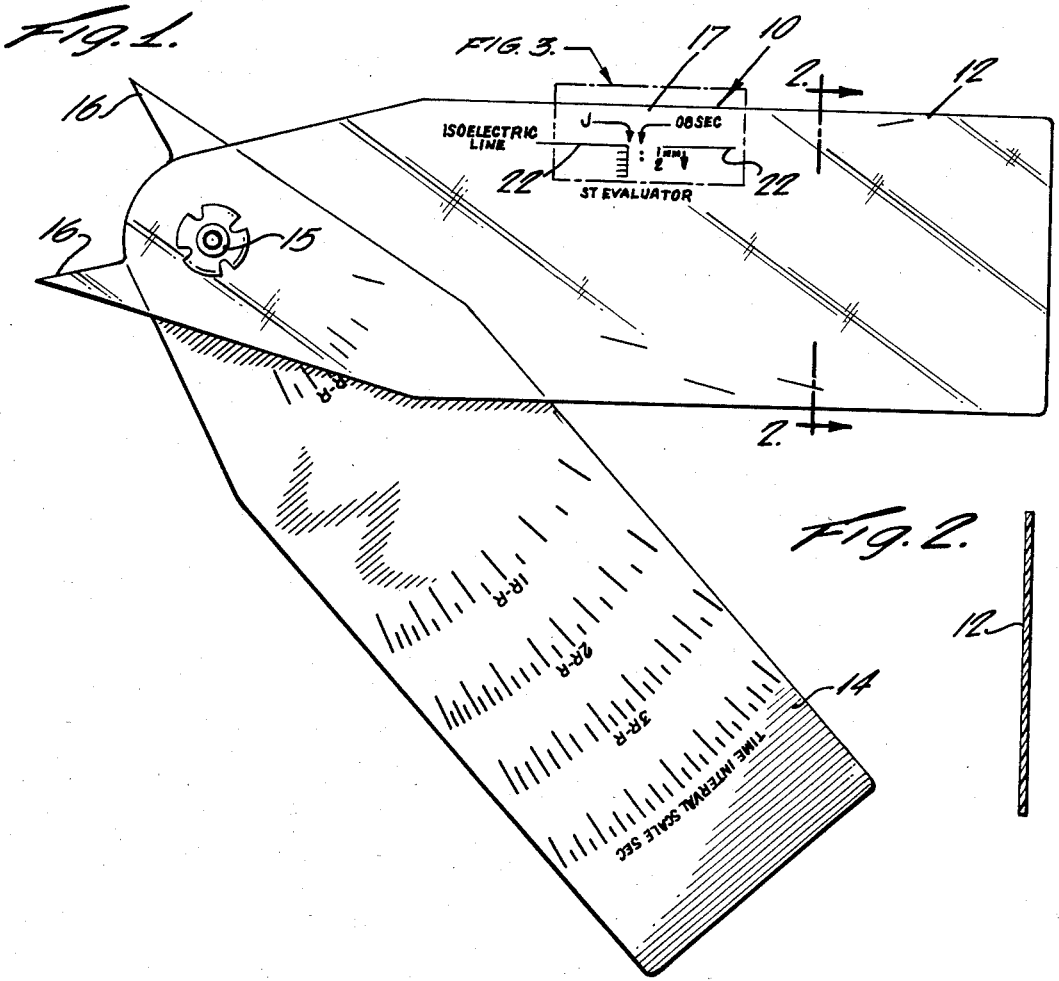
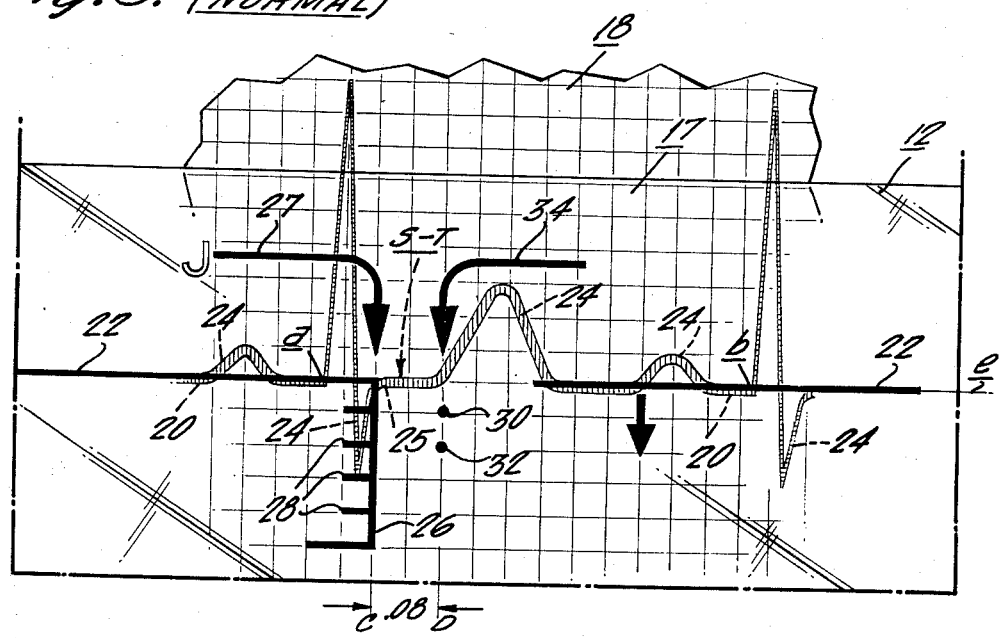

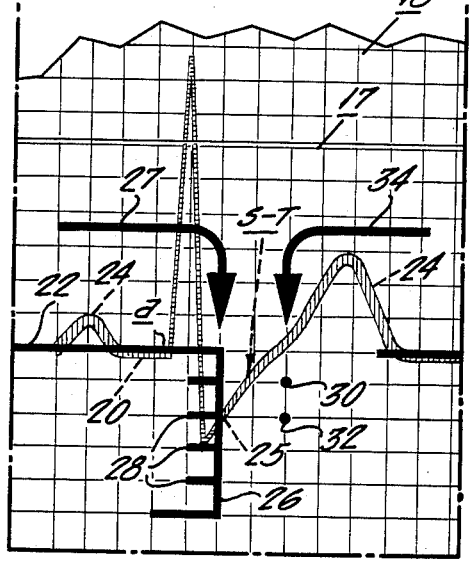
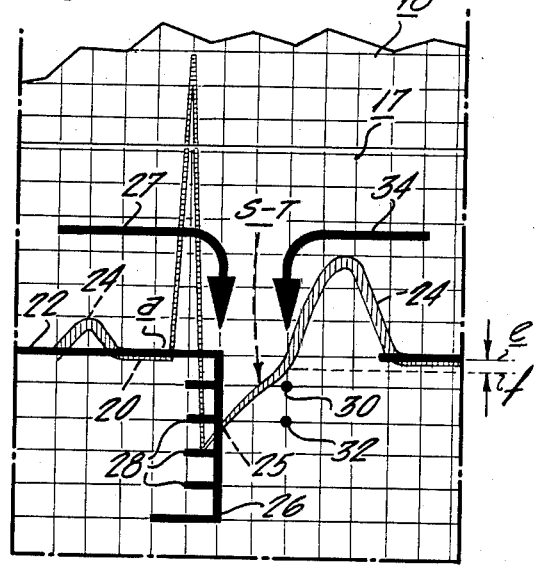
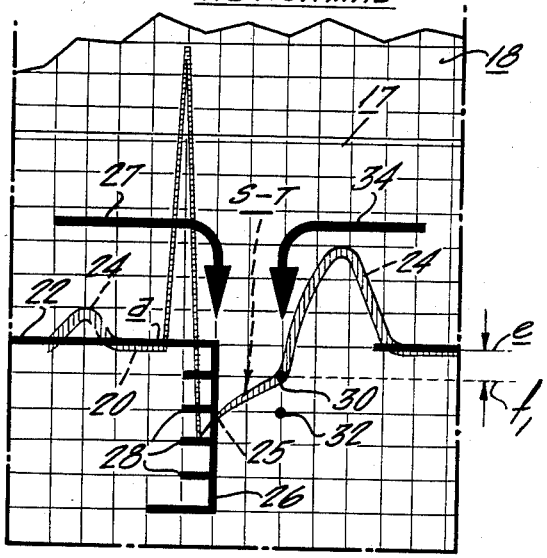
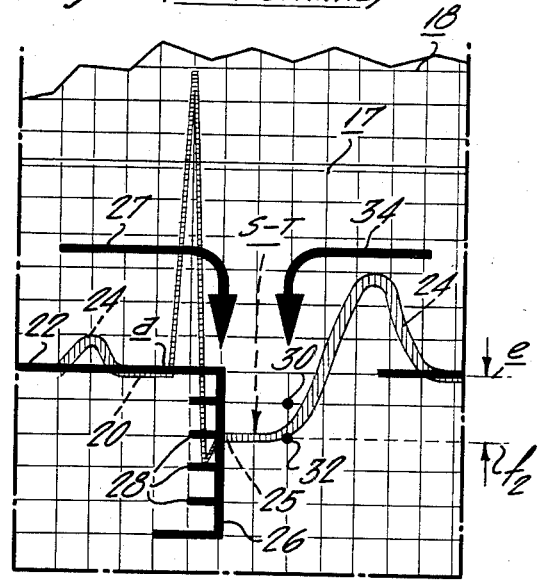

EXERCISE S-T SEGMENT EVALUATOR

BACKGROUND OF THE INVENTION

An electrocardiogram is a graphic representation of the electrical forces produced by the heart. It produces a diagnostic test which can be used by skilled and trained medical personnel to interpret various of the heart processes, sometimes identifying abnormal heart functioning and anatomy.

Numerous factors other than the heart itself can contribute to the record made. Among these are skin resistance, thickness of the chest, position of the heart in the thoracic cage, electrical interference, polarization, skeletal muscle tremors, infections, fear, shock, drugs, and many other factors. Included in the extrinsic factors is exercise.

Accordingly, and within limitations, a wide variety of exercise testing procedures have been employed in conjunction with electrocardiograms. The exercise stress test is a valuable part of cardiac evaluation. This test is performed with the patient exercising on a treadmill or bicycle ergometer and performing measured amounts of exercise of increasing intensity. During the test the heart rate, blood pressure and electrocardiogram are routinely recorded. The test ends at certain defined end points.

As is well known, the electrocardiograph waves have been correlated with the contracting heart. The P wave is associated with the atrial contraction, while the ventricular contraction is associated with the QRS complex and the T wave deflection. The septum and ventricles constituting the major muscle mass, are correspondingly responsible for the most important portion of the electrocardiogram. In addition, the atrial activity plays an important part in determining the basic rhythm of the heartbeat. The electrical impulse originates in the sinus node, travels to the atrionodal junction by way of internodal tracts as well as to the left atrium via interatrial tracts, next into the atrioventricular node and subsequently through the septum to the free ventricle walls. Sinus rhythm is characterized by recurrence of the P waves at regular intervals, followed in normal time sequence by QRS complexes and the T wave.

A normal electrocardiogram displays this sequence of waves on a chart or recorder paper, in some cases, or on a CRT display. Standardized equipment has produced uniformity in electrocardiograms, so that the chart is based on an X-Y coordinate system in which the isoelectric or reference base line travels from left to right on the graph, with standard 0.04 second intervals marked. Displacement above and below the isoelectric line is marked in one mm lines, so that the grid presents squares which are one mm or 0.04 seconds on a side.

The electrocardiogram reports the activity of the heart in terms of electric currents. Each mechanical contraction, atrial or ventricular, is associated with two electrical processes. The first process is activation or depolarization, during which the electrical charges on the surface of the muscle cell change from positive to negative. Repolarization, or return to the resting state, then follows with resultant replacement of the positive surface charges. Depolarization of the ventricles is a rapid affair, represented electrocardigraphically by the QRS complex; repolarization of the ventricles is slower and is designated by the T wave. The S-T segment represents the period when all parts of the ventricles are in the depolarized state. The S-T segment begins at the J-point and ends at the beginning of the T wave. Beyond this basic description, countless volumes have been written on the truly amazing amount of information which can be learned from various tests associated with electrocardiograms.

As previously mentioned, exercise, and exercise testing, is one factor which influences the electrocardiogram. A normal resting electrocardiogram can be obtained even though the patient has coronary atherosclerotic heart disease. In patients with angina pectoris, the resting electrocardiogram may be normal in about 70% of cases.

Exercise tests are only to be performed under the supervision of and in the presence of a physician who will monitor the tests and, of course, stop them immediately on signs of heart difficulties for the patient. Even when no physical symptoms are noticed by the patient, either due to insensitivity, preoccupation with test, nervousness, or whatever, heart damage can be occurring during the test and therefore the physician is highly anxious to monitor the test.

A most important electrocardiographic criteria of a positive response to the exercise test involve S-T segment changes. As the heart rate increases with exercise, the oxygen requirement of the heart muscle increases. The lack of oxygen to heart muscle as it is needed is the hallmark of coronary heart disease. If the coronary arteries get narrowed for whatever reason, they still might supply enough blood for a heart at rest rate, such as 60 or 70 beats per minute. But, as the rate increases to 120, or 130 or higher, the heart no longer receives enough oxygen in the blood. At that point, changes occur in the cardiac complex. Most meaningful is the S-T segment change, which is considered the hallmark of coronary disease and has the most diagnostic significance.

One of the most significant techniques of exercise testing is to accelerate the heart rate under controlled conditions and review electrocardiogram results, particularly the S-T segment, to see if the slope becomes more horizontal and depressed. During the testing, it should be, and is, kept in mind that evaluation of the S-T segment as it deviates from normalcy must be done at the time of the test, quickly and accurately, so that prompt medical care can be instituted if needed. Later analysis of the electrocardiograms in great detail and under suitable conditions to derive the most knowledge is of course one of the goals of the test. Primary, on sight analysis of the changes in S-T segments, must be done however, to give a first, safe diagnosis of the test. Because of this, quick accurate reading and evaluation of the normalcy of an S-T segment of an electrocardiogram is essential.

SUMMARY OF THE PRESENT INVENTION

Accordingly, it has now been discovered that a device, and method for its use, is available for quick accurate read of S-T segments of electrocardiograms taken in an exercise test program. The device is admirably suited for use by a physician during the critical testing sequences, so that deviations from the normalcy can immediately be diagnosed for prompt first treatment if needed. Confident assurance that nothing immediate needs to be done is also now possible with the aid of this invention.

The invention consists of a transparent overlay which is placed on the electrocardiogram to be studied. The overlay, preferably constructed from clear plastic, includes a horizontal line which is used as a reference line, to be placed over the isoelectric line of the electrocardiogram. The overlay base also includes a vertical line perpendicular to and crossing the reference line. This line designates the J-point on the electrocardiogram. A first point mark is placed on the base locating a point 0.08 seconds after (or to the right of) the J-point line and one mm below the reference line. A second point mark is placed directly below the first mark. It locates a point 0.8 seconds after the J-point line and two mm below the reference line.

When the overlay is placed on an electrocardiogram, the reference line overlays or is on top of the isoelectric line or base line. The J-point line overlays or is on top of a J-point on the electrocardiogram. The S-T segment, which is that portion of the tracing from the J-point to the beginning of the T wave, then passes near one or both of the marks on the overlay. A physician or trained medical personnel under the supervision of a physician can readily interpret the normalcy of the S-T segment quickly, accurately, and without resort to calculations or measurements.

In a preferred embodiment, the J-point line on the overlay is provided with a plurality of one mm incremental marks down from the reference line, so that the degree of J-point depression can readily be observed. In this embodiment, the J-point and S-T segment are quickly evaluated so that the patient receives proper attention and assurance.

BRIEF DESCRIPTION OF THE DRAWINGS

FIG. 1 is a schematic view of the overlay device as part of a clear plastic base, which overlay has been placed on an electrocardiogram analyzer.

FIG. 2 is a section taken on line 2—2 of FIG. 1.

FIG. 3 is an enlarged partially sectioned schematic view of the overlay device which has been placed on an electrocardiogram.

FIG. 4, FIG. 5, FIG. 6 and FIG. 7 are enlarged schematic views of the overlay device in position on various electrocardiograms which illustrate various S-T segments and the relationship of the device to those S-T segments.

DESCRIPTION OF THE PREFERRED EMBODIMENT

As shown in FIG. 1, the device 10 generally is mounted on a transparent overlay base 12, which in this embodiment includes a second portion 14, pivotably mounted at 15 to form calipers 16. Overlay 17 is positioned appropriately so that it can be placed on an electrocardiogram in the manner hereinafter described. The base 12 is transparent, and as shown in FIG. 2, quite thin relative to the length and size of the base.

In FIG. 3, the overlay 17 has been placed on an electrocardiogram printout 18 of standard design. The electrocardiogram is, as has been stated, graph paper in which the distance between lines from left to right represents 0.04 seconds.

The distance vertically between lines is one mm. The isoelectric line 20 represents the base of zero activity line on the printout 18. Overlay 17 has a reference line 22 which is positionable to overlay the isoelectric line 20.

The electrocardiogram 18 has printed thereon a tracing line 24 which raises above and below isoelectric line 20 in response to the data produced during the test.

Tracing 24 describes successive QRS complexes such as one between points a and b. In each QRS complex is a J-point 25, which is easily and accurately recognized by anyone with proper training for use of and monitoring these tests. In FIG. 3, the J-point 25 is aligned with J-point line 26 on the base 17. This line 26 is perpendicular to the reference line 22, and in this embodiment is identified by the J-point line indicator 27. J-point line 26 also has line increments 28, which are one mm apart, so that the amount of J-point depression can be observed.

Also associated with the overlay 17 is a first point mark 30 which is 0.08 seconds after the J-point line 26 and one mm below the reference line 22. A second point mark 32 is positioned on overlay 17 directly below first mark 30, and is 0.08 seconds after the J-point line 26 and two mm below the reference line 22. Time line indicator 34 aids in locating the two points 30 and 32 when the overlay 17 is in use. In FIG. 3, the reference line 22 and J-point line 26 have been placed over isoelectric line 20 and J-point, as described. Tracing 24 shows an S-T segment which is not depressed from isoelectric line 20 and which is considered to be normal, such as what would be obtained in an at rest condition.

In FIG. 4, another normal test is observed, where the S-T segment has reached the isoelectric line 20 and is well above the first mark 30. This is a typical test result from an exercise test program. Trained observers would probably evaluate this result without need of additional study. In FIG. 7, the S-T segment is completely flat out, or depressed, and actually passes through the second mark 32. This result is clearly abnormal, and very likely would be observed as such without additional study. Nevertheless, the patient might be exhibiting other symptoms of distress because of the exercise, and use of the overlay device of this invention would confirm the substantial degree of departure from normalcy.

As is usually the case in medicine, as in life, however, results are seldom extremely clear cut but rather are in between. FIG. 5 indicates a test pattern where the S-T segment is close to but does not touch first mark 30. FIG. 6 illustrates a test pattern where the S-T segment is only slightly flatter, so that it does intersect point 30. By use of the overlay, preliminary screening indicates the former to be a normal condition, while the latter is borderline abnormal. Without the overlay, the evaluation with respect to S-T segment normalcy cannot be made quickly, accurately and safely.

In view of the thus described invention, variations and modifications to meet individual whim or particular need will become evident to others skilled in the art. The foregoing description is for illustration, and not for limitation, however, and the scope of the invention is set forth in the following claims.

What is claimed is:

1. An overlay device for use with an electrocardiogram to evaluate the normalcy of the S-T segment in an exercise test program, comprising: a transparent overlay base sized to be placed over the electrocardiogram; a reference line on said base positionable to overlay the isoelectric line of said electrocardiogram; a J-point line on said base perpendicularly crossing said reference line, said J-point line being positionable to overlay a J-point on said electrocardiogram; a first point mark on said base locating a point 0.08 seconds after said J-point line and one mm below said reference line; and a second point mark on said base directly below said first mark and locating a point 0.08 seconds after said J-point line and two mm below said reference line; whereby the location of the S-T segment with respect to the first and second point marks describes the normalcy of the S-T segment.

2. The device of claim 1, wherein said transparent overlay base is clear plastic.

3. The device of claim 1, which further includes a plurality of one mm incremental marks on said J-point line below said reference line, whereby the degree of J-point depression can be observed.

4. A method of evaluating the normalcy of an S-T segment of an electrocardiogram, comprising the steps of: placing a transparent overlay base on said electrocardiogram, said base having a reference line and a J-point line perpendicular thereto, a first point mark indicatng a point 0.08 seconds after said J-point line and one mm below said reference line, and a second point mark directly below the first mark and indicating a point 0.08 seconds after said J-point line and two mm below said reference line; aligning the reference line to overlay the isoelectric line of said electrocardiogram and simultaneously aligning said J-point line to overlay a J-point on said electrocardiogram; and locating by observation the S-T segment with respect to said first and second marks, whereby the normalcy of the S-T segment is evaluated.

5. The method of claim 4 which further includes the steps of: locating the S-T segment from an electrocardiogram taken at rest, locating the S-T segment from an electrocardiogram taken as part of exercise testing, and comparing the two locations of the S-T segments with respect to the first and second marks on said overlay base.

6. The method of claim 5 in which the step of locating the S-T segment with respect to the first and second marks is repeated for a plurality of electrocardiograms taken as part of an exercise testing program, whereby the normalcy of the S-T segment during the program is evaluated.

7. The method of claim 5 which further includes the step of applying an overlay base on which a plurality of one mm increment marks are located on said J-point line, said overlay base being placed such that the degree of J-point depression is observably measured along said increment marks.

* * * * *